(12) United States Patent
Oka et al.

(10) Patent No.: US 7,006,929 B2
(45) Date of Patent: Feb. 28, 2006

(54) SIGNAL DETECTING SENSOR PROVIDED WITH MULTI-ELECTRODE

(75) Inventors: Hiroaki Oka, Hirakata (JP); Nobuhiko Ozaki, Ikoma (JP); Hirokazu Sugihara, Katano (JP); Satoshi Konishi, Otsu (JP)

(73) Assignees: Matsushita Electric Industrial Co., Ltd., Osaka (JP); The Ritsumeikan Trust, Kyoto (JP)

( * ) Notice: Subject to any disclaimer, the term of this patent is extended or adjusted under 35 U.S.C. 154(b) by 61 days.

(21) Appl. No.: 10/479,938

(22) PCT Filed: Jun. 5, 2002

(86) PCT No.: PCT/JP02/05569

§ 371 (c)(1),
(2), (4) Date: Dec. 5, 2003

(87) PCT Pub. No.: WO02/099408

PCT Pub. Date: Dec. 12, 2002

(65) Prior Publication Data

US 2004/0167723 A1    Aug. 26, 2004

(30) Foreign Application Priority Data

Jun. 5, 2001    (JP)    .............................. 2001-170340

(51) Int. Cl.
*G06F 19/00*    (2006.01)
(52) U.S. Cl. .......................... 702/31; 702/31; 702/177; 702/189; 702/198; 435/287.1; 435/288.3; 204/403.01; 324/446; 324/692; 356/246
(58) Field of Classification Search .................. 702/21, 702/31, 189, 198; 435/287.1, 288; 204/403.01; 324/446, 692; 356/246
See application file for complete search history.

(56) References Cited

U.S. PATENT DOCUMENTS

| 4,264,728 A | | 4/1981 | Wilkins |
| 5,314,495 A | * | 5/1994 | Kovacs ........................ 623/25 |
| 5,378,343 A | * | 1/1995 | Kounaves et al. .......... 204/413 |

(Continued)

FOREIGN PATENT DOCUMENTS

JP    06-078889    3/1994

(Continued)

OTHER PUBLICATIONS

Brignac Jr., et al., 'Engineering in Genomics: A Proximal CCD Imaging System for High-Throughput Detection of Microarray-Based Assays', Mar. 1999, IEEE Engineering in Medicine & Biology, pp. 120-122.*

(Continued)

*Primary Examiner*—Marc S. Hoff
*Assistant Examiner*—Elias Desta
(74) *Attorney, Agent, or Firm*—Snell & Wilmer L.L.P.

(57) ABSTRACT

A sensor capable of simply and quickly measuring the electrical activities of a number of cells simultaneously and a device comprising the sensor and capable of detecting the signal transmission between subject cells are provided. The sensor comprises a plurality of electrodes provided on a substrate. The electrodes individually measure a signal generated by a biological sample held by each of the electrodes. Each of the electrodes comprises a depression for holding the biological sample, a throughhole which is in communication with the depression and penetrates to a rear side of the substrate, an electrode portion, and a drawing line from the electrode portion. The electrodes are arranged so that the samples held by the depressions electrically communicate with one another.

17 Claims, 11 Drawing Sheets

U.S. PATENT DOCUMENTS

| | | | |
|---|---|---|---|
| 5,387,329 A | * | 2/1995 | Foos et al. ............. 204/403.06 |
| 6,051,422 A | * | 4/2000 | Kovacs et al. ........... 435/287.1 |
| 6,193,864 B1 | * | 2/2001 | Leader et al. .......... 204/403.02 |
| 6,453,759 B1 | * | 9/2002 | Lebski et al. ............ 73/864.34 |
| 6,484,045 B1 | * | 11/2002 | Holker et al. ................ 600/345 |
| 6,682,649 B1 | | 1/2004 | Petersen, et al. |
| 2003/0080314 A1 | | 5/2003 | Nisch, et al. |

FOREIGN PATENT DOCUMENTS

| | | |
|---|---|---|
| JP | 06-296595 | 10/1994 |
| JP | 08-122326 | 5/1996 |
| JP | 09-289886 | 11/1997 |
| JP | 11-187865 | 7/1999 |
| WO | WO 99/28037 | 6/1999 |
| WO | WO 99/64559 | 12/1999 |

OTHER PUBLICATIONS

Austin et al., 'A New Technology for Quantifying Behavioral Activation in the Rodent', Nov. 2, 1997, IEEE/EMBS, pp. 2411-2414.*

"Multichannel Cell Membrane Potential Measuring System and Its Application to Cortical Development Study", by Hirokazu Sugihara, et al., National Technical Report, vol. 42, No. 2, Apr. 1996, pp. 112-119.

* cited by examiner

SIGNAL DETECTING SENSOR PROVIDED WITH MULTI-ELECTRODE

TECHNICAL FIELD

The present invention relates to a sensor for measuring electrophysiological characteristics of biological samples. The present invention also relates to a sensor device for artificially reconstructing a neural cell network and a sensor device applicable to simple and high-speed drug screening, and an intercellular network analyzing apparatus and a drug screening apparatus which comprise the sensor.

BACKGROUND ART

Drug screening has been conducted by measuring the electrical activity of a cell exposed to a drug. Typically, the electrical activity of a cell is measured by a patch clamp method, a method employing a fluorescent pigment or a light emitting indicator, or the like.

In the patch clamp method, a small portion (patch) of cell membrane, which is attached to a tip portion of a micropipette, is used to electrically record ion transport through a single ion channel protein. The patch clamp method is one of a few number of cell biological techniques which can be used to investigate the function of a single protein molecule in real time (see, e.g., Molecular Biology of the Cell, 3rd Ed., Garland Publishing, Inc., New York, 1994, Japanese Version, translation supervised by Keiko Nakamura et al., pp. 181–182, 1995, Kyoikusha). The electrical activity of a cell is also measured by a combination of a light emitting indicator or a fluorescent pigment, which emits light in response to a change in the concentration of a particular ion, with a state-of-the-art image processing method (e.g., a fluorescent image of a cell is taken by a CCD camera or the like to monitor intracellular ion transport).

The patch clamp method requires special techniques for preparation of a micropipette and the like. Therefore, the patch clamp method is not suitable for screening a large quantity of candidate compounds for a drug at high speed. The method using a fluorescent pigment or the like can screen a large quantity of candidate compounds for a drug at high speed. However, this method requires a step of staining cells. During measurement, pigments cause high background noise, and the fluorescence intensity decreases with time, resulting in poor signal to noise ratio (S/N). There is a demand for a cell potential measuring device with which data having substantially the same quality as that obtained by a patch clamp method can be obtained and which can be performed simply, quickly and automatically, as with the fluorescent pigment method.

An object of the present invention is to improve conventional apparatuses for measuring the electrical activities of cells as described above and to provide a sensor capable of simply and quickly measuring the electrical activities of a number of cells simultaneously and a device capable of detecting signal transmission between subject cells.

DISCLOSURE OF THE INVENTION

The present inventors have obtained an electrophysiological measurement device in which a micromachining technique is used to form a small hole having a diameter or a side in the range from 0.5 to 5 mm in a substrate device and with which a number of samples can be simultaneously measured with accuracy close to the level of conventional patch clamp methods.

The present invention relates to a sensor, comprising a plurality of electrodes provided on a substrate, in which the plurality of electrodes individually measure a signal generated by a biological sample held by each of the electrodes.

Each of the electrodes comprises a depression for holding the biological sample, a throughhole which is in communication with the depression and penetrates to a rear side of the substrate, an electrode portion, and a drawing line from the electrode portion. The electrodes are arranged so that the samples held by the depressions electrically communicate with one another.

Preferably, the signal is a signal which responds to a stimulus applied to the biological sample held by one of the plurality of electrodes.

Preferably, the plurality of electrodes are arranged so that there is an interval of 20 $\mu$m between a center of each electrode.

Preferably, the substrate is made of a material selected from the group consisting of silicon wafer, Teflon, polystyrene, polycarbonate, polyethyleneterephthalate, polyimide, acrylic, silicone rubber, PMDS and elastomer.

Preferably, the electrode portion is made of a material selected from the group consisting of gold, platinum, silver chloride, silver, platinum black, and ITO.

Preferably, the depression for holding the biological sample has a depth of 1 to 10 $\mu$m and an opening portion diameter of 10 to 50 $\mu$m, and the throughhole has a diameter of 2 to 10 $\mu$m.

Preferably, the biological sample is a neuron, the neurons held by the electrodes reconstruct a neural cell network in accordance with the arrangement of the plurality of electrodes.

Preferably, the stimulus is applied via the electrode portion of at least one of the plurality of electrodes.

Preferably, the sensor further comprises a counter electrode with respect to the electrode. When the biological sample is a neuron, a membrane potential of the neuron can be fixed.

Preferably, the sensor further comprises a reference electrode.

Preferably, the reference electrode is a ring-like electrode having a diameter of 100 to 10000 $\mu$m which is made of a ribbon-like member having a line width of 1 to 1000 $\mu$m.

Preferably, the electrode portion and the drawing line are patterned on the rear side of the substrate and are drawn to a periphery of the substrate.

Preferably, the sensor further comprises a means for holding the biological samples within the plurality of electrodes where the biological sample is tightly attached to the electrode.

Preferably, the means for holding the biological sample is a suctioning line.

Preferably, the sensor comprises a means for controlling the means for holding the biological sample.

The present invention also relates to an intercellular network analyzing apparatus, comprising: the above-described sensor; a cell accommodating means provided on the sensor; a means for maintaining the sensor having the cell accommodating means in cell growth conditions; a means for holding the sample on each electrode of the sensor where the sample is tightly attached to the electrode; a means for obtaining an electrical signal from each electrode of the sensor; and a means for processing the electrical signal.

The present invention also relates to a high-speed drug screening apparatus, comprising: the above-described sensor; a cell accommodating means provided on the sensor; a means for maintaining the sensor having the cell accommodating means in cell growth conditions; a means for moving the sensor having the cell accommodating means; a means for holding the sample on each electrode of the sensor where the sample is tightly attached to the electrode; a means for obtaining an electrical signal from each electrode of the sensor; and a means for processing the electrical signal.

With the above-described configuration of the sensor of the present invention, noise caused by opening and closing of an ion channel can be made possible, which cannot be achieved by conventional extracellular recording. Analysis of signal transmission in a neural cell network artificially reconstructed on the sensor can be made possible.

BRIEF DESCRIPTION OF THE DRAWINGS

Note that reference numerals shown in FIGS. 1 to 11 represent members below.

1: substrate, 2: cell accommodating means, 3: depression, 5: opening portion of a hole, 7: hole, 8: conductor line, 9: measuring electrode, 10: substrate terminal portion, 11: reference electrode, 15: suctioning line, 20: suctioning line attachment, A: culturing apparatus, B: moving means, C: signal detecting apparatus, D: signal drawing cable, E: signal processing section.

BEST MODE FOR CARRYING OUT THE INVENTION

Figure 1:
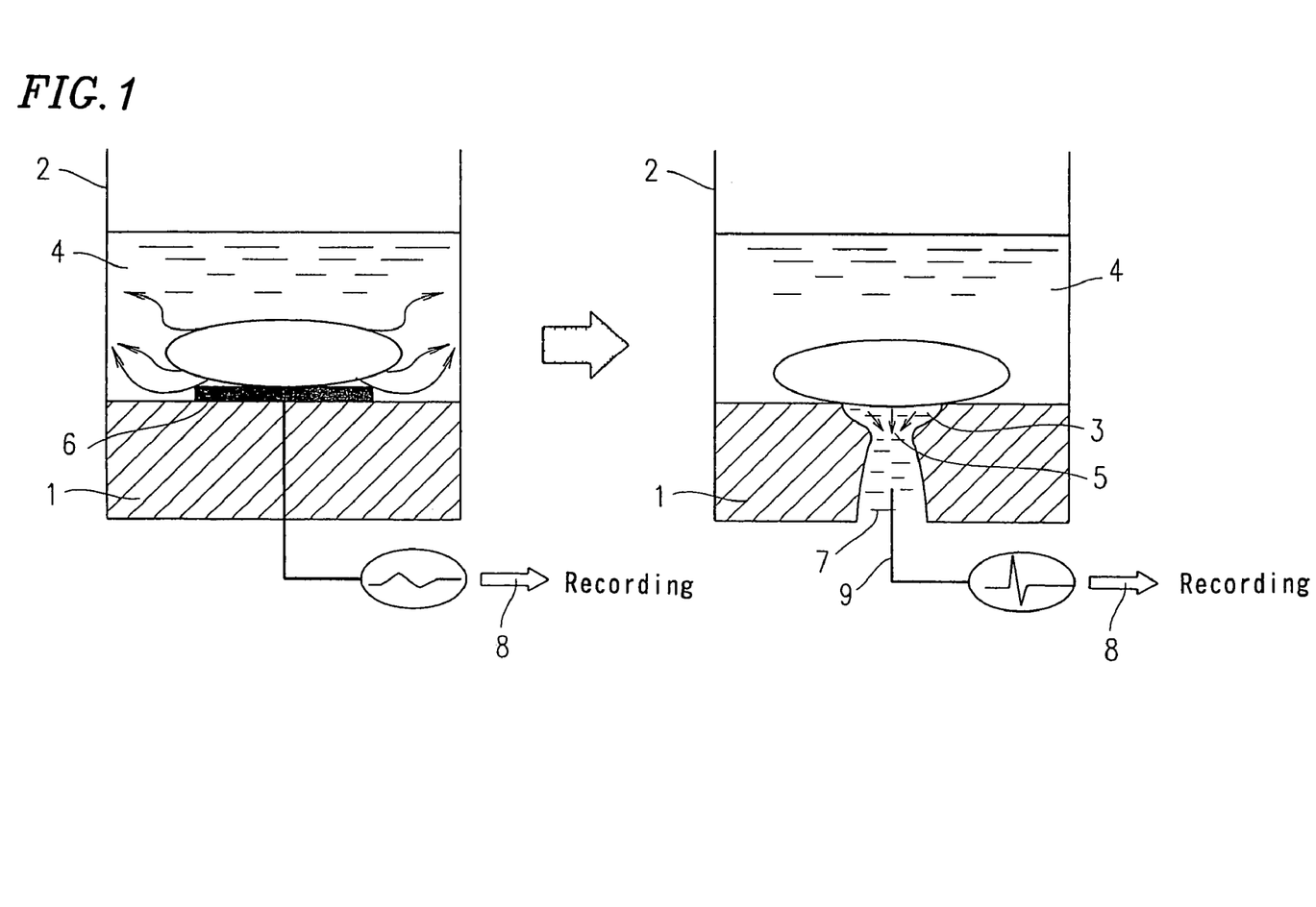
FIG. 1 is a diagram showing a principle of measurement and structure of a sensor of the present invention, comparing with a conventional sensor with a microelectrode. A part of the structure of the sensor of the present invention is shown to the right of FIG. 1. A conventional microelectrode is shown to the left of FIG. 1.

FIG. 1 schematically shows an outline of a principle of measurement and a structure of an electrode of a sensor according to the present invention. Culture medium is provided in a cylindrical container 2 placed on a substrate 1, which is used to accommodate biological samples, such as cells or the like. An electrode structure comprising a conventional planar microelectrode 6, on which a cell is placed, is shown to the left of FIG. 1. An exemplary electrode structure according to the present invention is shown to the right of FIG. 1, in which a subject cell, which is represented by an ellipse at the middle of the cylindrical container 2, is captured or held by a depression 3 which is a part of a cell holding means provided in the substrate 1. The cell holding means comprises the depression 3 provided in the substrate 1, a through hole 7 which is in communication with the depression 3 via an opening portion 5, and a suctioning line (not shown).

The example to the right of FIG. 1 shows that a measuring electrode 9 which is a signal detecting means is placed in the throughhole 7. The measuring electrode 9 is linked via a wiring 8 to a signal detecting section (not shown). The throughhole 7 forms a part of a suctioning section which is in communication with a suctioning means, such as a suctioning pump or the like, and is linked to a cell suctioning means (not shown). The cell suctioning means suctions a cell held by the depression 3 so that the cell membrane of the cell is tightly attached to the substrate 1, whereby electrical signals obtained via the cell membrane within the depression 3 are not leaked into the culture medium in a well as indicated with arrows in FIG. 1.

Note that a structure unit comprising a depression provided on a substrate as described above and a measuring electrode provided in a throughhole, which is in communication with the depression, is herein defined as an "electrode" or an "electrode structure". A device arrangement comprising the "electrode" structure and a substrate supporting the electrode structure, a member for accommodating a cell, and a drawing line connected to the electrode, and the like, is defined as a "sensor".

The example to the right of FIG. 1 shows that a part of a cell is fitted into the opening portion of the depression 3. The cell is tightly attached to and held by the substrate 1 so that electrical signals generated by the cell do not leak into the culture medium 4. In contrast, in the case of the conventional planar microelectrode shown to the left of FIG. 1, most of the electrical signals emitted by the cell leak into the culture medium 4 as indicated by the arrows in FIG. 1, so that the signal detection sensitivity is significantly reduced.

The electrode structure shown to the right of FIG. 1 is further provided with a reference electrode, as required. The measuring electrode 9 is used to measure an electrical signal of a cell with reference to a reference potential of the reference electrode. Typically, the reference electrode is a wire whose section has a diameter of about 100 μm to about 1000 μm and which is made of a material, such as gold, platinum, silver-silver chloride, or the like. The reference electrode may be in any size and shape, as required. Further, one or more reference electrodes may be provided per well, as required, whereby the measurement accuracy of the cell potential may be improved.

Such a sensor comprising one or more depressions is formed by a conventional micromachining technique.

(Embodiments)

Figure 2:
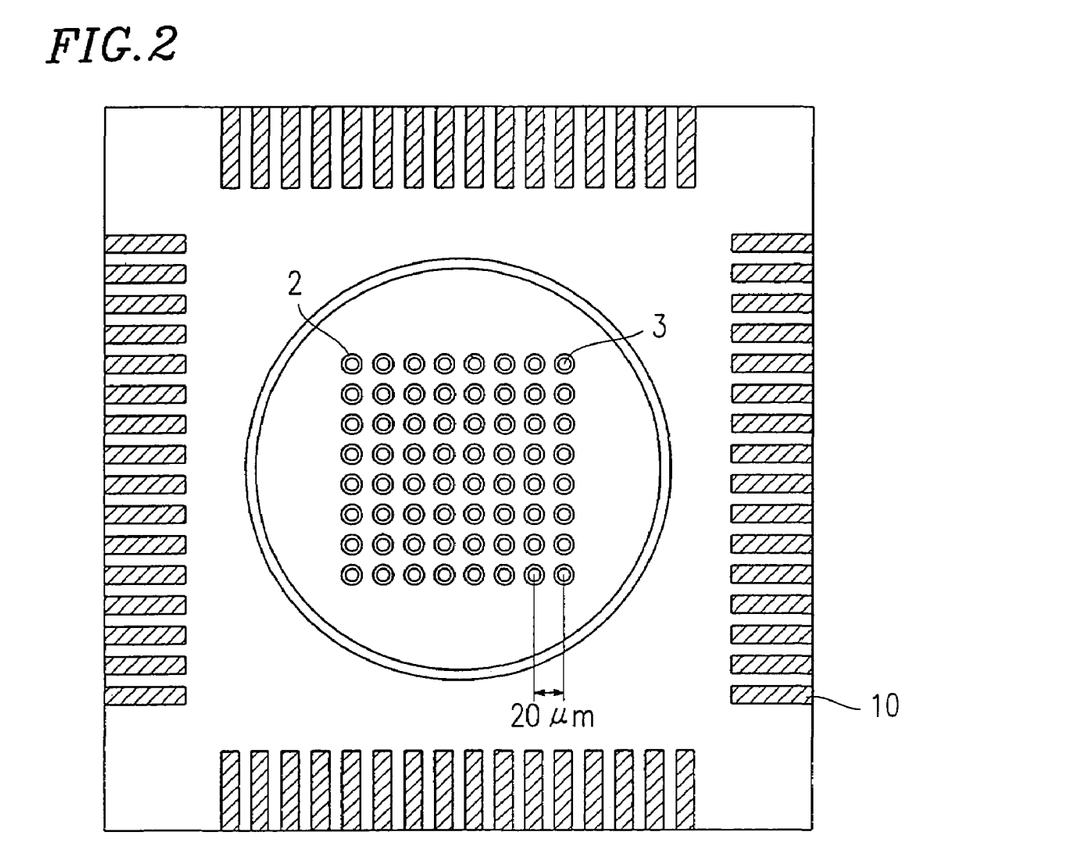
FIG. 2 is a plane view of the sensor of the present invention.

FIG. 2 shows an exemplary sensor according to an embodiment of the present invention. FIG. 2 is a plane view of an example of an embodiment of the present invention. In the embodiment, electrodes each comprising a depression whose opening portion has a diameter of about 10 μm are arranged in a matrix of 8×8, where an interval between the center of each electrode is about 20 μm. Reference numeral 2 indicates a container for accommodating culture medium and a cell placed on the electrode. A total of 64 substrate terminal portions 10 each connected to a measuring electrode of a corresponding electrode are provided on a periphery of a substrate (size: 30 mm×30 mm), where each substrate terminal portion is isolated from the other electrodes or conductor lines (note that drawing lines are not shown).

Figure 3:
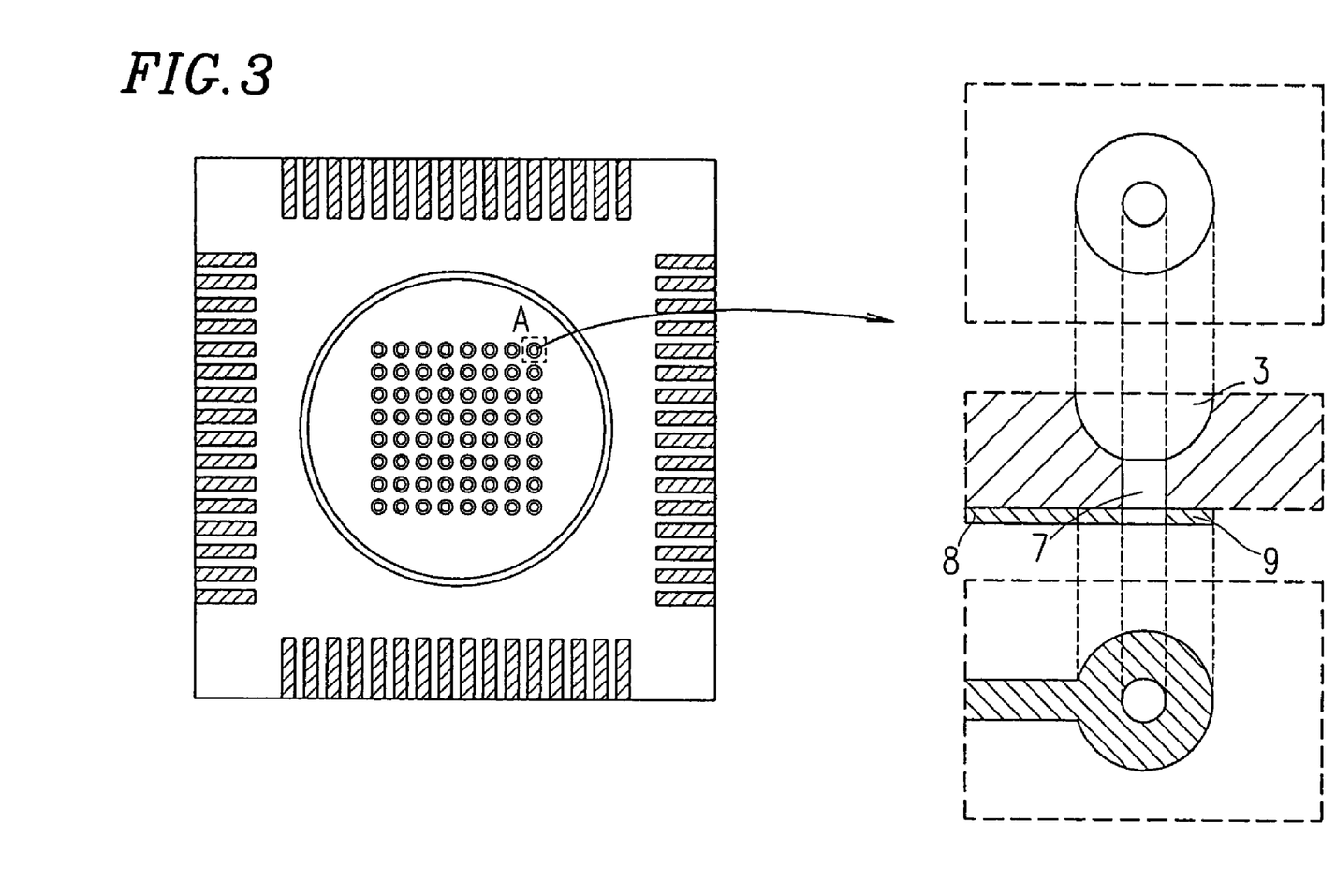
FIG. 3 shows a plane view of the sensor of the present invention, and an enlarged, plane view, cross-sectional view, and rear side view indicating a structure of an electrode which is a part of the sensor.

FIG. 3 is an enlarged view of an electrode structure of a sensor according to an example of an embodiment of the present invention. In the example of FIG. 3, each electrode comprises a depression 3 whose opening portion has a diameter of about 10 µm. A measuring electrode 9 (also herein referred to as an electrode portion of the electrode) is patterned on a rear side of the substrate by sputtering or the like. The measuring electrode 9 is drawn via a signal drawing line 8 up to the periphery of the substrate. A throughhole 7 whose opening portion has a diameter of about 3 µm is provided at a middle portion of a bottom side of the depression. Three diagrams shown to the right of FIG. 3 are enlarged views of a single electrode constituting a sensor, enlarging a portion surrounded by a dotted line and indicated by A to the left of FIG. 3, corresponding to a plane view, a cross-sectional view taken along a straight line passing through a middle of the depression 3, and a rear side view in this order from the top.

Figure 4:
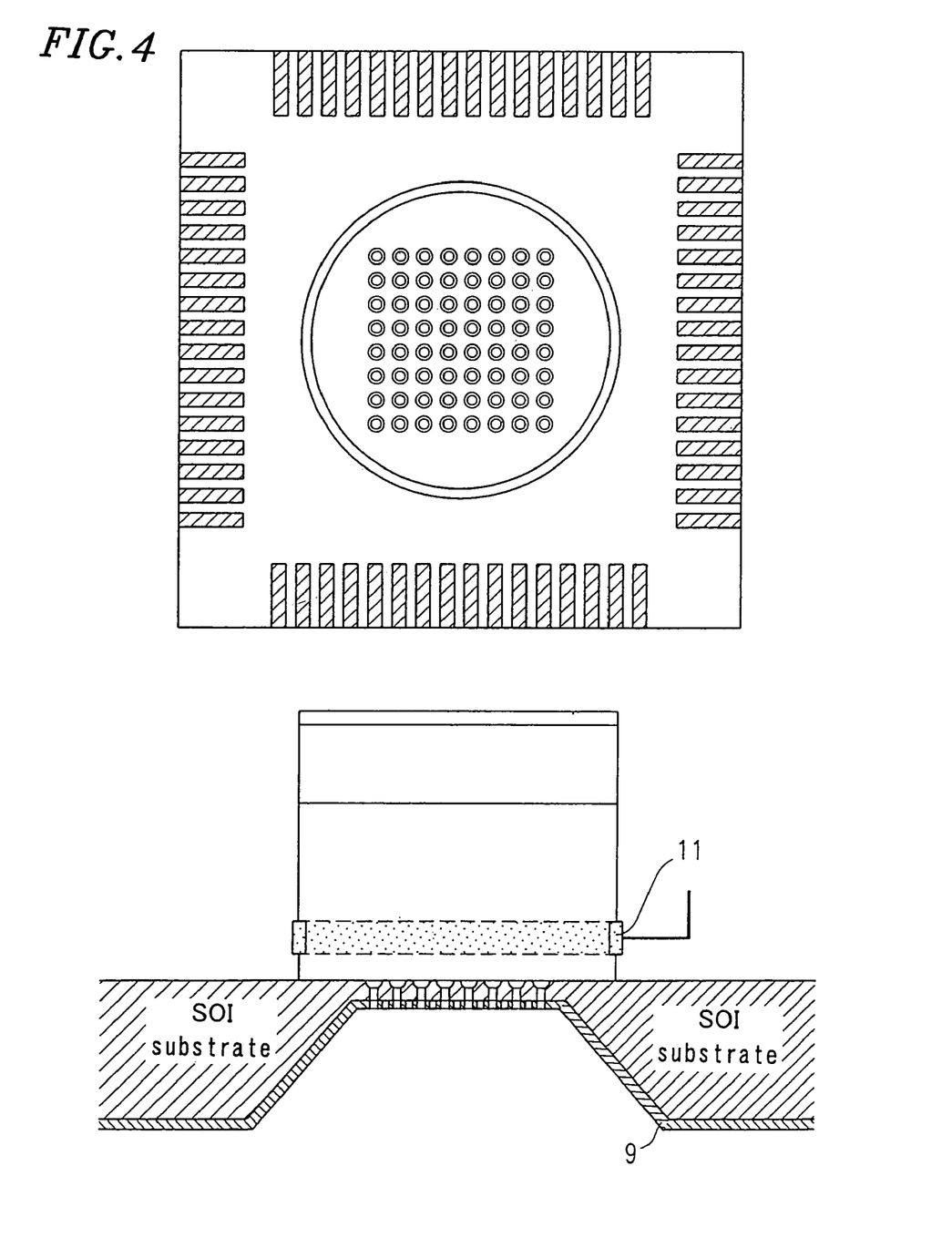
FIG. 4 shows a plane view indicating an outline of a variation of the sensor of the present invention, and an enlarged, cross-sectional view indicating a structure of an electrode which is a part of the sensor.

FIG. 4 shows an exemplary sensor according to an embodiment of the present invention. In this embodiment, an electrode comprises a measuring electrode 9, a depression 3, and a throughhole 7. The measuring electrode 9 is patterned on a rear side of a SOI substrate so that the measuring electrode 9 contacts the throughhole 7. A ring-like reference electrode 11 having a diameter of 100 µm, which is made of a ribbon-like member having a line width of 100 µm, is provided on a wall of a container for accommodating a biological sample.

Figure 5:
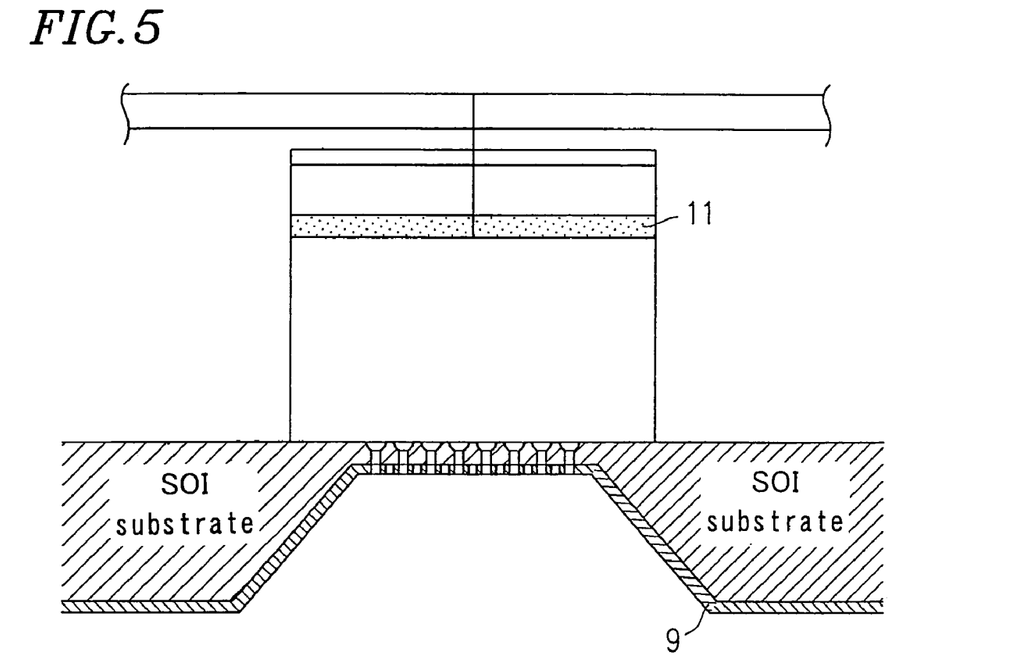
FIG. 5 shows a cross-sectional view indicating an outline of a variation of a sensor of the present invention.
Figure 6:
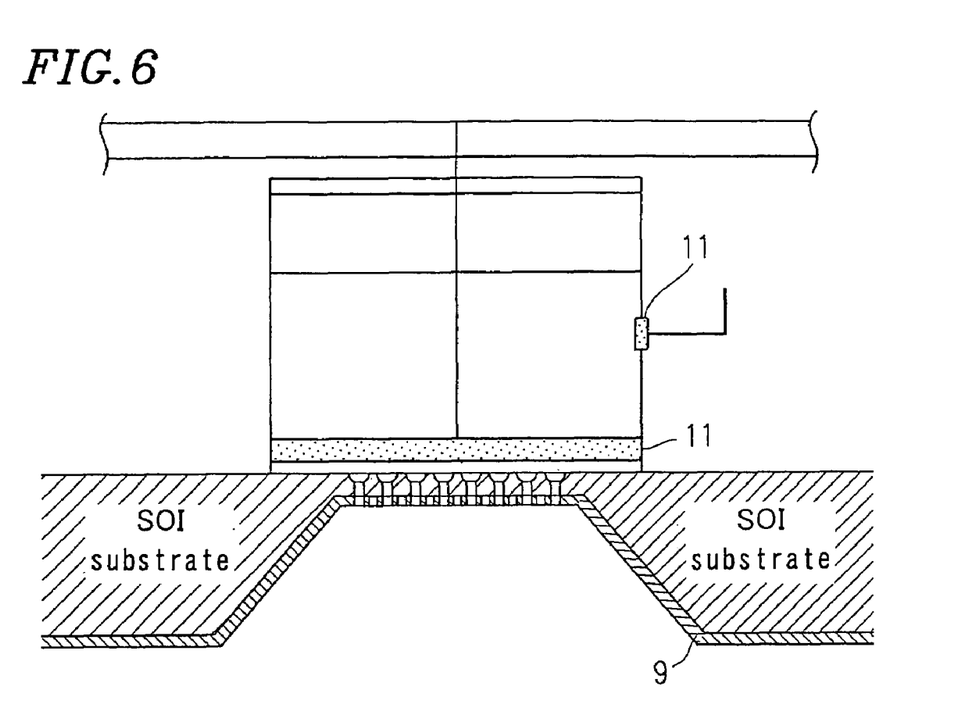
FIG. 6 shows a cross-sectional view indicating an outline of a variation of a sensor of the present invention.

FIG. 5 shows an example in which a reference electrode is provided within a container for accommodating a cell. FIG. 6 shows an example in which a reference electrode is provided on a portion of a wall of a container for accommodating a cell and a bottom portion of the container. The form and position of the reference electrode may be selected depending on the purpose of measurement and a biological sample to be measured.

The reference electrode functions as a counter electrode with respect to the measuring electrode and may fix the membrane potential of a cell held therewith (the potential of a cell membrane is set to an arbitrary value). A weak electrical pulse (e.g., a 100-Hz polarization pulse) may be applied between the reference electrode and the measuring electrode so that the ion permeability of the cell membrane of a cell held in a well can be improved.

Figure 7:
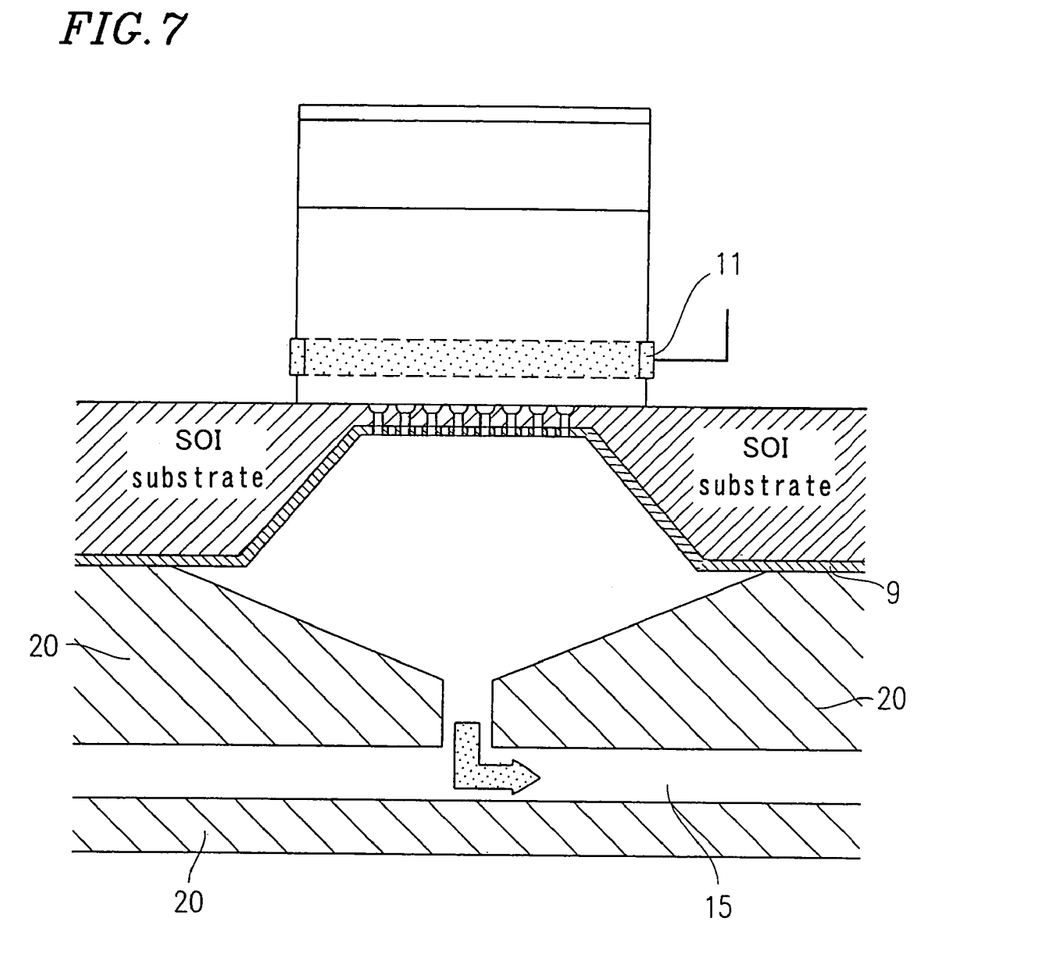
FIG. 7 shows a cross-sectional view indicating an outline of a variation of a sensor of the present invention.

FIG. 7 shows a sensor comprising a suctioning line 15 according to an embodiment of the present invention. The suctioning line 15 is provided within a suctioning line attachment 20 provided on a rear side of a substrate. The suctioning line 15 is linked to a suctioning means (not shown), such as an aspirator or the like, so that the tightness between a cell and an electrode structure can be improved. The suctioning line attachment 20 is typically made of an acrylic, PMDS, a silicone rubber, or the like. The suctioning line attachment 20 covers a measuring electrode and is attached to the rear side of the substrate.

Note that only an electrolyte (typically, Krebs ringer solution) suctioned by the suctioning means is present in a space in the vicinity of the measuring electrode on the rear side of the sensor of the present invention. Therefore, electrolyte solution present on the rear side of the sensor of the present invention is not more than 1 to 10 µl including electrolyte solution filling the throughhole. Further, it is not particularly necessary that the entire cell suctioning system is filled with electrolyte, as long as an electrical change in a cell can be detected by the measuring electrode.

Figure 8:
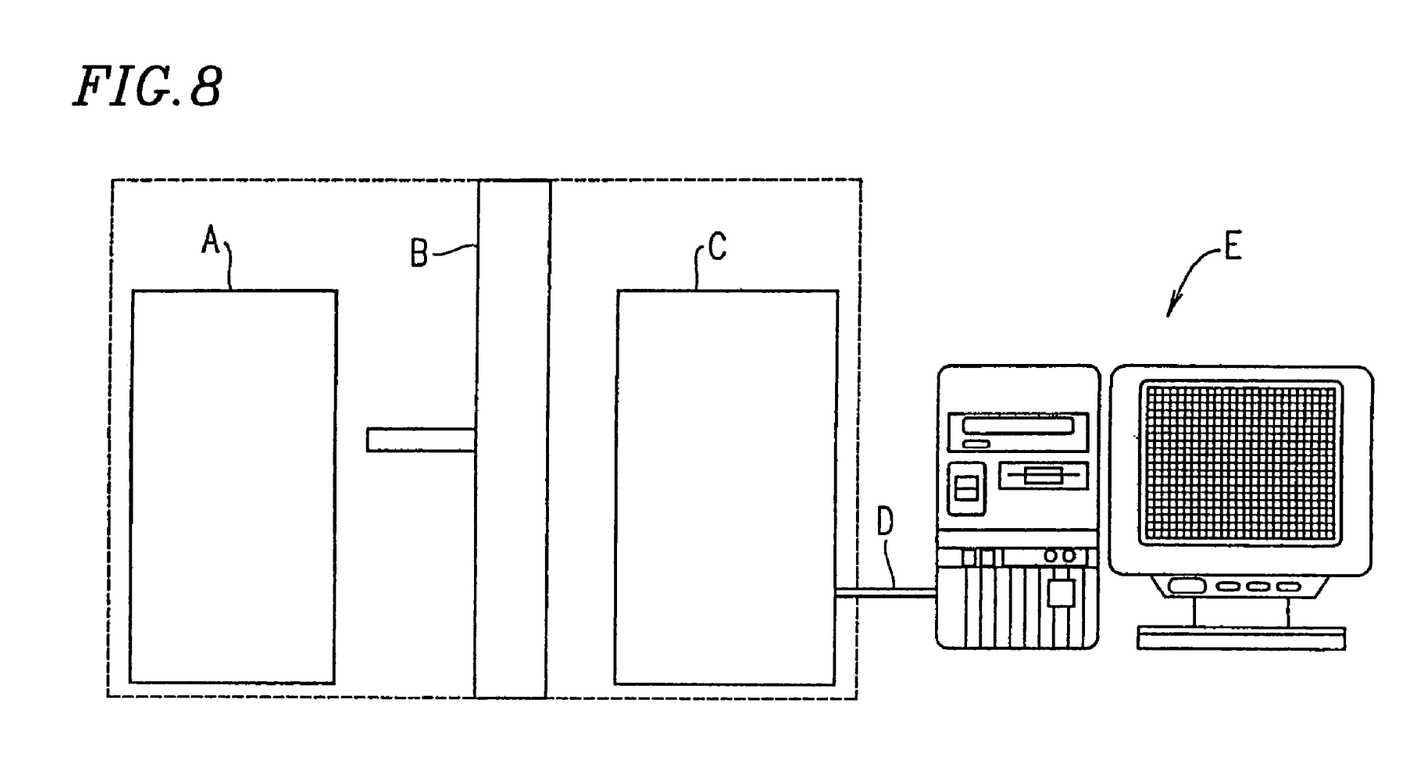
FIG. 8 is a schematic diagram showing a configuration of an intercellular network analyzing apparatus of the present invention.

FIG. 8 schematically shows an exemplary configuration of an intercellular network analyzing apparatus or a high-speed drug screening apparatus comprising the above-described sensor of the present invention. The configuration of FIG. 8 is described below. A: a culturing apparatus for maintaining a sensor having a cell accommodating means in cell growth conditions. An environment suitable for the growth and maintenance of subject biological samples is provided. B: a means for transferring the sensor from the culturing apparatus to a signal detecting apparatus C. For example, a robot arm may be employed. C: the signal detecting apparatus. The signal detecting apparatus comprises a means for injecting or removing a subject drug solution, such as a reagent dispensing multipipette, a sensor comprising the above-described multielectrode, an aspirator or a suctioning pump, and the like. D: a signal drawing cable. E: a signal processing apparatus (computer).

The above-described components can be linked using a means known in the art and this process is not described in detail.

An intercellular network apparatus incorporating the sensor of the present invention comprises the sensor, a cell accommodating means provided on the sensor, a means for maintaining cell growth conditions, a means for holding the sample where the sample is tightly attached to each electrode of the sensor, a means for obtaining an electrical signal from each electrode of the sensor, and a means for processing the electrical signal.

The intercellular network apparatus may further comprise a stimulus applying means for applying a current to an arbitrary electrode on the sensor, and a microscope or an image capturing means for displaying a state of a cell cultured on the sensor. The cell accommodating means typically holds a solution for maintaining cells.

The means for maintaining the cell growth conditions typically maintains an environment accommodating the cell so as to provide temperature, humidity, pH, and gas composition optimum to cell growth. The means for processing the electrical signal typically takes a signal from each electrode of the sensor.

A high-speed drug screening apparatus incorporating the sensor of the present invention comprises the sensor, a cell accommodating means provided on the sensor, a means for maintaining the cell growth conditions, a means for moving the sensor on which the cell accommodating means is provided, a means for holding the sample on each electrode in the sensor where the sample is tightly attached to the electrode, a means for obtaining an electrical signal from each electrode of the sensor, and a means for processing the electrical signal.

The high-speed drug screening apparatus may further comprise a means for injecting or removing a solution to or from the cell accommodating container located at an arbitrary position of the sensor.

The cell accommodating means typically holds a solution for maintaining cells. The means for maintaining the cell growth conditions typically maintains an environment accommodating the cell so as to provide temperature, humidity, pH, and gas composition optimum to cell growth.

The means for processing the electrical signal typically obtains a signal from each electrode of the sensor and subjects the signals to statistical processing.

EXAMPLES

The present invention will be described by way of examples. The examples below illustrate the present invention and do not limit the present invention.

Example 1

Neurons were prepared from the cerebral cortex of gestation day 17 rat embryos and were suspended in Dulbecco's modified medium, and were dispensed into each container of a sensor comprising 64 electrodes and containers as shown in FIG. 3 at a concentration of $5 \times 10^5$ cells/ml, followed by culturing for two weeks. As a result, an artificial neural cell network was reconstructed on the sensor.

The sensor containing the reconstructed neural cell network was used as follows. An apparatus having the configuration of FIG. 8 was used to apply a constant voltage stimulus (50 $\mu$V) to one of the 64 electrodes (an electrode at (row 5, column 6) in FIG. 9) via the electrode portion so that the constant voltage stimulus was applied to a cell on the sensor. The transmission of the stimulus was measured by detecting cell potentials at the remaining 63 electrodes.

Figure 9:
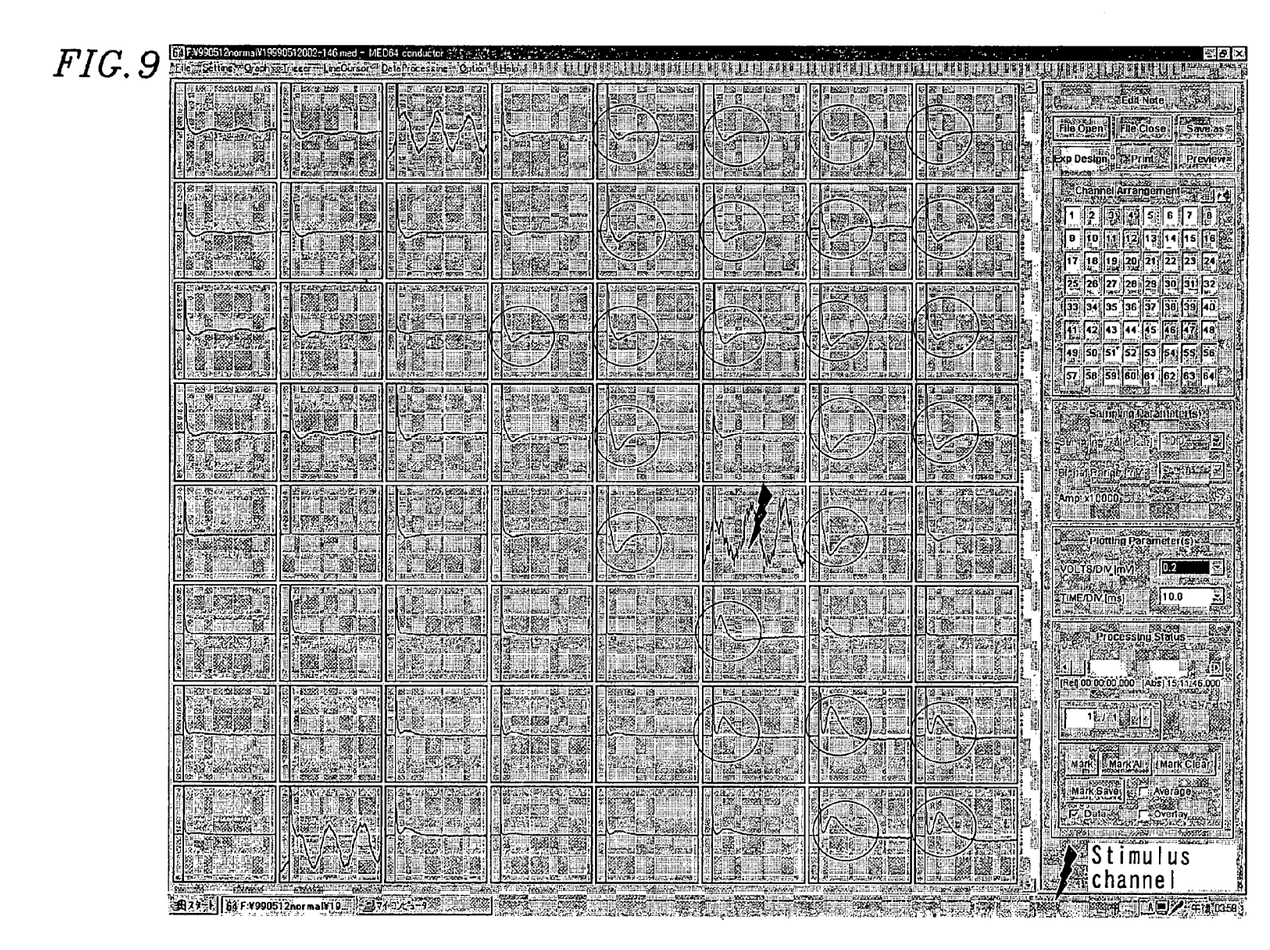
FIG. 9 is a diagram showing results of a test using a cell potential measuring device of the present invention.

The results are shown in FIG. 9. FIG. 9 is a hard copy of the signal processing apparatus (computer screen). As shown in FIG. 9, associated signal transmission was observed in encircled channels, i.e., 24 of the 63 electrodes. Thus, reconstruction of a neural cell network was confirmed.

Example 2

Figure 10:
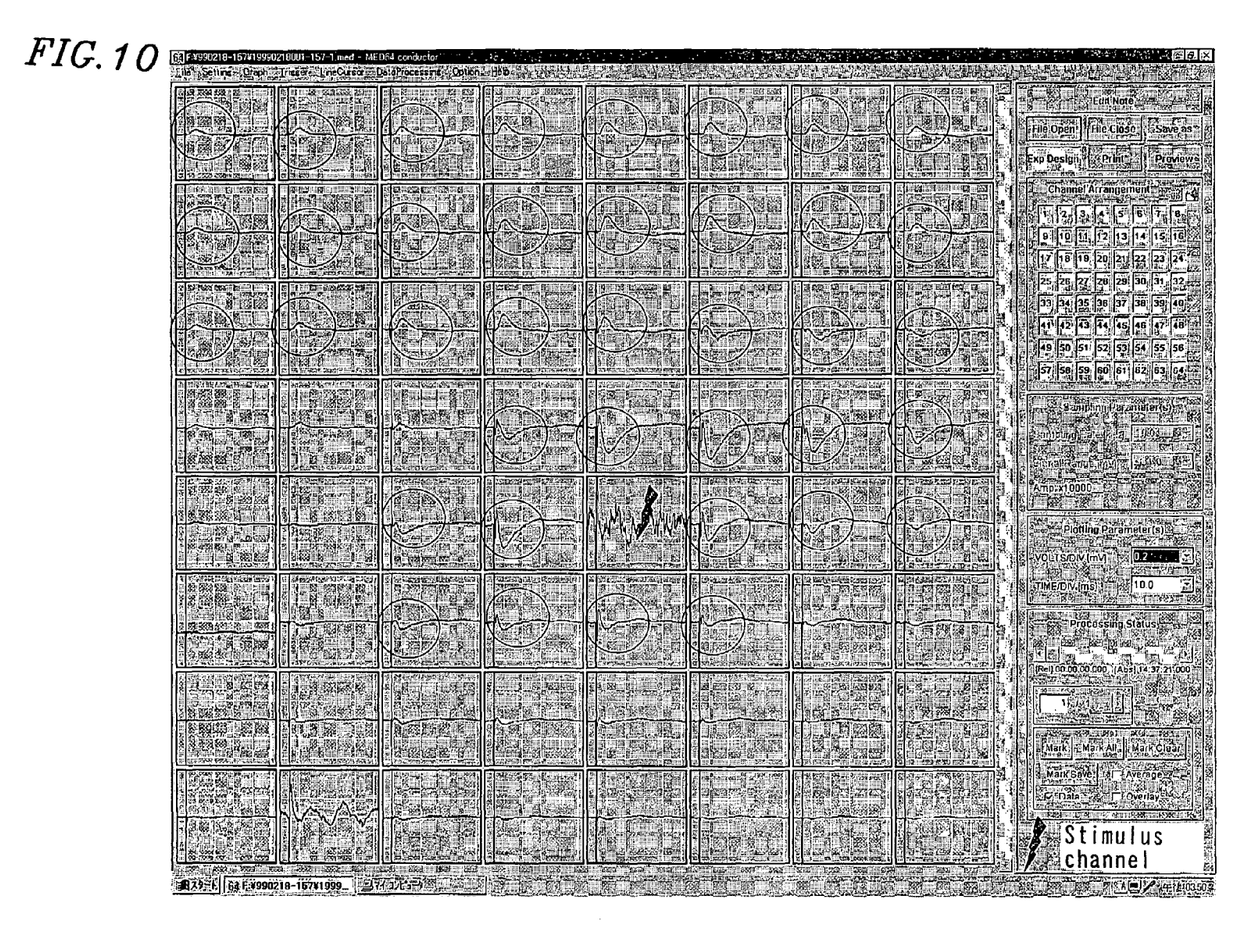
FIG. 10 is a diagram showing results of a test using the cell potential measuring device of the present invention.

As shown in FIG. 10, stimulus transmission was measured by detecting cell potentials at the remaining 63 electrodes in the same manner as that of Example 1, except that a constant voltage stimulus was applied to an electrode at (row 5, column 5). As a result, associated signal transmission was observed in 38 of the 63 electrodes as shown in FIG. 10.

Example 3

Figure 11:
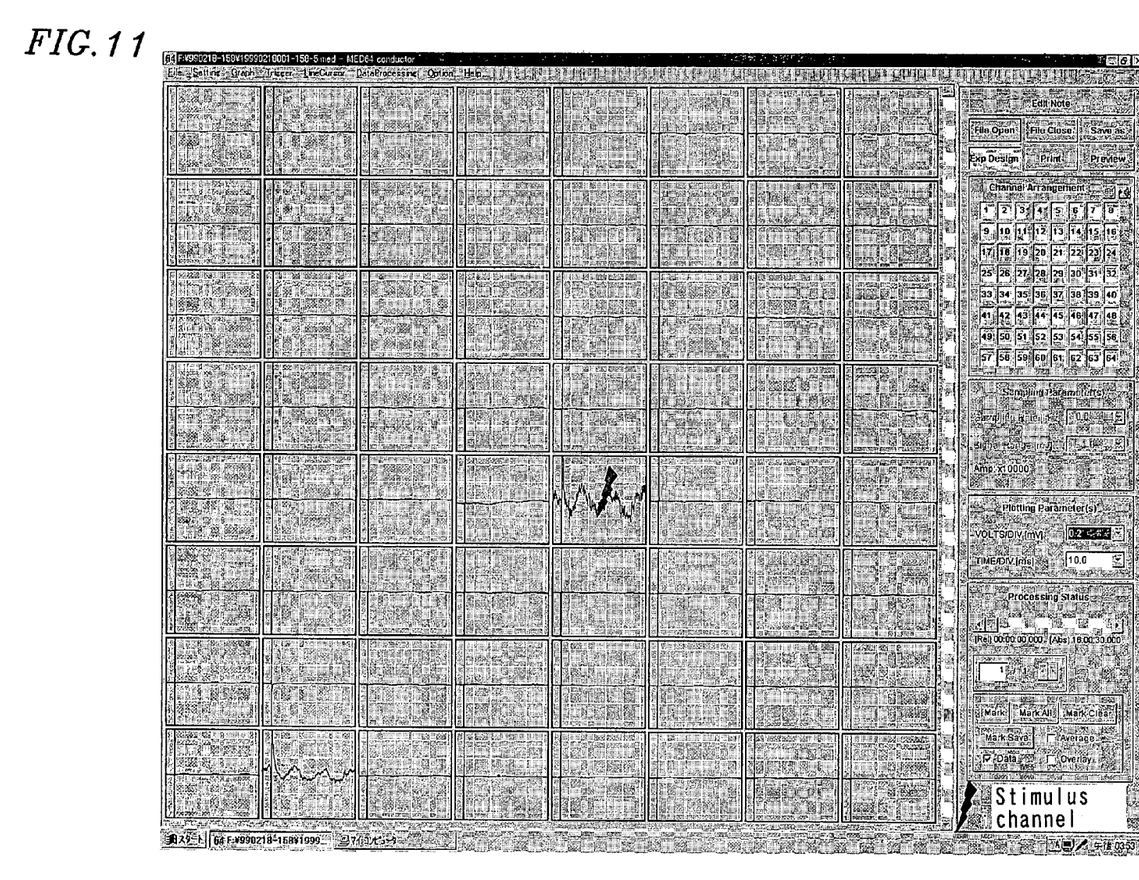
FIG. 11 is a diagram showing results of a test using the cell potential measuring device of the present invention.

A neural cell network reconstructed as in Examples 1 and 2 was treated with 40 $\mu$M DNQX (6,7-Dinitroquinoxaline-2,3(1H,4H)-dione) for 10 minutes. As in Example 2, a constant voltage stimulus was applied to a cell on a sensor. The transmission of the stimulus was measured by detecting cell potentials at the remaining 63 electrodes. As a result, a response was not observed at any of the electrodes (FIG. 11). This result shows that DNQX completely blocked a reaction which was otherwise mediated by a synapse in response to the constant voltage stimulus.

The above-described three examples showed the sensor of the present invention can be used to measure the signal transmission of an artificially reconstructed neural cell network. In addition, the sensor of the present invention has been capable of measuring the frequency of opening and closing of a potential-sensitive ion channel of a cell by fixing the membrane potential of the cell.

INDUSTRIAL APPLICABILITY

A sensor capable of simply and quickly measuring the electrical activities of a number of cells simultaneously and a device capable of detecting the signal transmission between subject cells, are provided.

The device of the present invention overcomes drawbacks of a conventional patch clamp method which requires a high level of skill or a conventional fluorescent pigment method which includes a number of testing steps and has a poor S/N ratio. With the device of the present invention, it is possible to provide an apparatus capable of screening drug candidate compounds simply and quickly, and dramatically reduce the long time required for conventional drug screening. Further, since such an apparatus does not require a high level of special skill and can automatically collect data and process a signal, anybody can easily measure a cell potential.

What is claimed is:

1. A sensor, comprising a plurality of electrodes provided on a substrate, wherein the plurality of electrodes individually measure a signal generated by a biological sample held by each of the electrodes, each of the electrodes comprises a depression for holding the biological sample, a throughhole which is in communication with the depression and penetrates to a rear side of the substrate, an electrode portion, and a drawing line from the electrode portion, and the electrodes are arranged so that the samples held by the depressions electrically communicate with one another.

2. A sensor according to claim 1, wherein the signal is a signal which responds to a stimulus applied to the biological sample held by one of the plurality of electrodes.

3. A sensor according to claim 1, wherein the plurality of electrodes are arranged so that there is an interval of 20 $\mu$m between a center of each electrode.

4. A sensor according to claim 1, wherein the substrate is made of a material selected from the group consisting of silicon wafer, Teflon, polystyrene, polycarbonate, polyethyleneterephthalate, polyimide, acrylic, silicone rubber, PMDS and elastomer.

5. A sensor according to claim 1, wherein the electrode portion is made of a material selected from the group consisting of gold, platinum, silver chloride, and silver.

6. A sensor according to claim 1, wherein the depression for holding the biological sample has a depth of 1 to 10 $\mu$m and an opening portion diameter of 10 to 50 $\mu$m, and the throughhole has a diameter of 2 to 10 $\mu$m.

7. A sensor according to claim 1, wherein the biological sample is a neuron, the neurons held by the electrodes reconstruct a neural cell network in accordance with the arrangement of the plurality of electrodes.

8. A sensor according to claim 2, wherein the stimulus is applied via the electrode portion of at least one of the plurality of electrodes.

9. A sensor according to claim 1, further comprising a counter electrode with respect to the electrode, wherein when the biological sample is a neuron, a membrane potential of the neuron can be fixed.

10. A sensor according to claim 7, further comprising a reference electrode.

11. A sensor according to claim 10, wherein the reference electrode is a ring-like electrode having a diameter of 100 to 10000 $\mu$m which is made of a ribbon-like member having a line width of 1 to 1000 $\mu$m.

12. A sensor according to claim 1, wherein the electrode portion and the drawing line are patterned on the rear side of the substrate and are drawn to a periphery of the substrate.

13. A sensor according to claim 1, further comprising a means for holding the biological samples within the plurality of electrodes where the biological sample is tightly attached to the electrode.

14. A sensor according to claim 13, wherein the means for holding the biological sample is a suctioning line.

15. A sensor according to claim 14, comprising a means for controlling the means for holding the biological sample.

16. An intercellular network analyzing apparatus, comprising: a sensor according to claim 1; a cell accommodating means provided on the sensor; a means for maintaining the sensor having the cell accommodating means in cell growth conditions; a means for holding the sample on each electrode of the sensor where the sample is tightly attached to the electrode; a means for obtaining an electrical signal from each electrode of the sensor; and a means for processing the electrical signal.

17. A high-speed drug screening apparatus, comprising: a sensor according to claim 1; a cell accommodating means provided on the sensor; a means for maintaining the sensor having the cell accommodating means in cell growth conditions; a means for moving the sensor having the cell accommodating means; a means for holding the sample on each electrode of the sensor where the sample is tightly attached to the electrode; a means for obtaining an electrical signal from each electrode of the sensor; and a means for processing the electrical signal.

* * * * *